(12) United States Patent
Vaitekunas

(10) Patent No.: US 7,553,284 B2
(45) Date of Patent: Jun. 30, 2009

(54) FOCUSED ULTRASOUND FOR PAIN REDUCTION

(76) Inventor: Jeffrey J. Vaitekunas, 17650 Hyde Park Ave., Lakeville, MN (US) 55044

( * ) Notice: Subject to any disclaimer, the term of this patent is extended or adjusted under 35 U.S.C. 154(b) by 277 days.

(21) Appl. No.: 11/048,974

(22) Filed: Feb. 2, 2005

(65) Prior Publication Data

US 2006/0184069 A1    Aug. 17, 2006

(51) Int. Cl.
*A61N 7/00* (2006.01)
*A61B 8/00* (2006.01)
(52) U.S. Cl. .............................. 600/439; 601/2; 606/27; 606/32; 606/41
(58) Field of Classification Search ............... 601/2, 601/3; 600/439; 606/27, 32, 41; 514/816, 514/818
See application file for complete search history.

(56) References Cited

U.S. PATENT DOCUMENTS

| 5,807,285 | A | 9/1998 | Vaitekunas |
| 5,873,844 | A | 2/1999 | Campero |
| 6,083,156 | A * | 7/2000 | Lisiecki ..................... 600/301 |
| 6,432,067 | B1 | 8/2002 | Martin |
| 6,508,774 | B1 | 1/2003 | Acker |
| 6,656,136 | B1 | 12/2003 | Weng |
| 7,305,264 | B2 | 12/2007 | Larson |
| 2002/0055736 | A1 | 5/2002 | Horn |
| 2003/0004439 | A1 | 1/2003 | Pant |
| 2003/0018255 | A1 | 1/2003 | Martin |
| 2003/0191396 | A1 | 10/2003 | Sanghvi |
| 2003/0233045 | A1 | 12/2003 | Vaezy |
| 2004/0039312 | A1 | 2/2004 | Hillstead |
| 2004/0106880 | A1 | 6/2004 | Weng |
| 2004/0162507 | A1 | 8/2004 | Govari |
| 2004/0162550 | A1 | 8/2004 | Govari |
| 2005/0240126 | A1 * | 10/2005 | Foley et al. ..................... 601/2 |
| 2006/0041277 | A1 | 2/2006 | Deem |
| 2006/0058671 | A1 | 3/2006 | Vitek |
| 2006/0058678 | A1 | 3/2006 | Vitek |

FOREIGN PATENT DOCUMENTS

WO    WO 2004/100850    11/2004

* cited by examiner

*Primary Examiner*—Brian Cassler
*Assistant Examiner*—Parikha S Mehta
(74) *Attorney, Agent, or Firm*—Jeffrey J. Vaitekunas

(57) ABSTRACT

Methods and devices that provide ultrasonic energy used to cause one or more nerves to become dysfunctional. A nerve to be treated is placed in the focal zone of ultrasonic energy emitted by ultrasound transducer. A first level of ultrasonic energy is provided to the nerve using the ultrasound transducer, the first level sufficient to stimulate the nerve. A verification is made that the desired nerve is being stimulated by the first level of ultrasonic energy. For example, the patient may be asked to confirm that the ultrasonically stimulated nerve corresponds to the pain that is affecting the patient. Subsequent to verifying the stimulated nerve is the nerve desired for the reduction of pain, a second level of ultrasonic energy is delivered to the nerve using the ultrasound transducer, the second level of ultrasonic energy sufficient to cause nerve dysfunction.

12 Claims, 9 Drawing Sheets

FOCUSED ULTRASOUND FOR PAIN REDUCTION

FIELD OF THE INVENTION

The present invention relates, in general, to ultrasonic energy used to reduce or eliminate pain and, more particularly, to methods and devices that provide focused ultrasound for temporary or permanent pain reduction.

BACKGROUND OF THE INVENTION

The fields of ultrasonics and stress wave propagation encompass applications ranging from non-destructive testing in materials science, to beer packaging in high-volume manufacturing. Diagnostic ultrasound uses low-intensity energy, typically in the 0.1-to-20-MHz region, to determine pathological conditions or states by imaging. Therapeutic ultrasound produces a desired bio-effect, and can be divided further into two regimes, one, typically in the region of 20 kHz to 200 kHz, sometimes called low-frequency ultrasound, and the other, typically in the region from 0.2 to 10 MHz, where the wavelengths are relatively small so focused ultrasound can be used for therapy. At high intensities of energy, this application is referred to as HIFU for High Intensity Focused Ultrasound.

Examples of known therapeutic ultrasound applications are: HIFU for tumor ablation and lithotripsy, low-frequency/high amplitude phacoemulsification, thrombolysis, liposuction, neural surgery, and the use of ultrasonic scalpels for cutting and coagulation. In low-frequency ultrasound, direct contact of an ultrasonically active end-effector or surgical instrument delivers ultrasonic energy to tissue, creating bio-effects. Specifically, the instrument produces heat to coagulate and cut tissue, and cavitation to help dissect tissue planes. Other bio-effects include: ablation, accelerated bone healing and increased skin permeability for transdermal drug delivery.

At the tip of the end-effector, the energy is delivered to tissue to create several effects within the tissue. These include the basic gross conversion of mechanical energy to both frictional heat at the blade-tissue interface, and bulk heating due to viscoelastic losses within the tissue. In addition, there may be the ultrasonically induced mechanical mechanisms of: cavitation, microstreaming, micro-jet formation and sonoluminescence.

Ultrasonic medical devices are used for the safe and effective treatment of many medical conditions. Ultrasonic surgical instruments, and particularly solid core ultrasonic instruments, are advantageous because they may be used to cut and/or coagulate organic tissue using energy in the form of mechanical vibrations transmitted to a surgical end-effector at ultrasonic frequencies. Ultrasonic vibrations, when transmitted to organic tissue at suitable energy levels and using a suitable end-effector, may be used to cut, dissect, or cauterize tissue. Such instruments are particularly suited for use in minimally invasive procedures, such as endoscopic or laparoscopic procedures, wherein the end-effector is passed through a trocar to reach the surgical site.

SUMMARY OF THE INVENTION

The present invention is directed to methods and devices that provide ultrasonic energy used to cause one or more nerves to become dysfunctional. A nerve to be treated is placed in the focal zone of an ultrasonic wave front emitted by ultrasound transducer. A method of pain reduction in accordance with embodiments of the present invention involves targeting the focal zone of a high intensity focused ultrasound transducer on a nerve. A first level of ultrasonic energy is provided to the nerve using the ultrasound transducer, the first level sufficient to stimulate the nerve. A verification is made that the desired nerve is being stimulated by the first level of ultrasonic energy. For example, the patient may be asked to confirm that the ultrasonically stimulated nerve corresponds to the pain that is affecting the patient. Subsequent to verifying the stimulated nerve is the nerve desired for the reduction of pain, a second level of ultrasonic energy is delivered to the nerve using the ultrasound transducer, the second level of ultrasonic energy sufficient to cause nerve dysfunction.

Other embodiments of methods in accordance with the present invention further involve providing ultrasound energy from the ultrasound transducer, starting at a zero or quiescent amplitude, and increasing the amplitude until the response of the stimulated nerve is detected. The response of the stimulated nerve may be detected by a patient acknowledging that the stimulated nerve is the nerve desired for the reduction of pain, such as by pressing a switch, verbal acknowledgement, or other acknowledgement mechanism. Other embodiments verify the response of the stimulated nerve by detecting a measured response of the stimulated nerve to the first level of ultrasonic energy, such as by using electrophysiology measurements, brain wave detection, or other measuring methodologies. For example, the measured response may be an electrophysiolical measurement of the nerve distal to the targeted focal zone or a measure of neural activity consistent with neural activity associated with a localized pain of a patient.

Providing a second level of ultrasonic energy to the nerve may involve providing ultrasound energy from the ultrasound transducer at a level sufficient to denature the nerve, thereby causing permanent nerve dysfunction. The patient may be placed into a non-conscious state prior to delivering the second level of ultrasound energy to mitigate any pain associated with the higher level of energy delivery. In further embodiments of methods in accordance with the present invention, a compressive force is provided to the nerve as the denatured nerve congeals. The ultrasound energy from the ultrasound transducer may be transcutaneously applied, intra-abdominally applied, laparoscopically applied, or directly applied to a nerve bundle.

Other embodiments involve generating an ultrasound image of the area proximate the nerve, wherein targeting the focal zone of the ultrasound transducer on the nerve involves targeting the nerve using the ultrasound image.

Embodiments of devices in accordance with the present invention include an ultrasonic therapy transducer configured to target a focal zone of the transducer on neural tissue. Therapy circuitry may be configured to provide a first level of ultrasonic energy to the neural tissue using the ultrasonic therapy transducer, the first level sufficient to stimulate the neural tissue. Level adjusting circuitry may be configured to adjust the therapy circuitry to a second level of ultrasonic energy, the second level of ultrasonic energy sufficient to cause nerve dysfunction of the neural tissue.

Systems may further include a switch configured to provide a confirmation signal to the ultrasonic system, thereby enabling the second level of ultrasonic energy to be provided by the therapy circuitry. An ultrasonic imaging system may be configured to provide an image of tissue surrounding the neural tissue, the image comprising an indicator that indicates the focal zone of the ultrasound therapy transducer.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

The features of the invention may be set forth with particularity in the appended claims. The invention itself, however, both as to organization and methods of operation, together with further objects and advantages thereof, may best be understood by reference to the following description, taken in conjunction with the accompanying drawings in which:

Figure 1A:
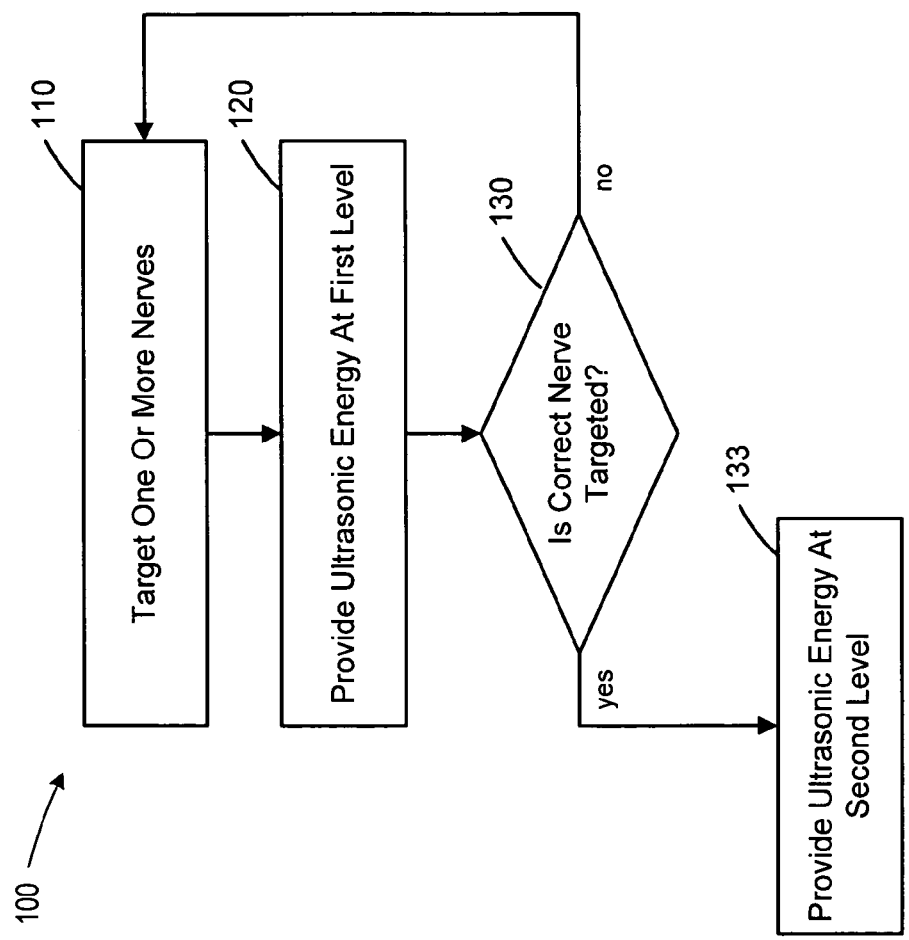
FIG. 1A illustrates a method of pain reduction in accordance with embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF THE INVENTION

In the following description of the illustrated embodiments, references are made to the accompanying drawings, which form a part hereof, and in which is shown by way of illustration various embodiments in which the invention may be practiced. It is to be understood that other embodiments may be utilized, and structural and functional changes may be made without departing from the scope of the present invention.

It is known to use ultrasound or ultrasonic energy in medical procedures and that ultrasonic energy can be useful in medical procedures performed in proximity to nerves. However, teachings on the topic disclose conflicting conclusions. A first school suggests using ultrasonic energy to selectively dissect around nerves describing the ability of ultrasonic energy to remove tissue while sparing nerves associated with the tissue.

A second school reports nerve damage due to ultrasonic energy and specifically mentions nerve damage up to 1.5 mm ahead of an ultrasonic energy applying tip. U.S. Pat. No. 5,807,285, hereby incorporated by reference, describes using a low-frequency solid-core ultrasonic surgical device to provide temporary nerve dysfunction, such as for vagotomies or other procedures.

There are a wide variety of instances when it would be desirable to be able to make a given nerve dysfunctional. A non-limiting, non-exhaustive list of examples include: twitches, chronic pain, and surgical procedures such as vagotomies to correct ulcers. Chronic pain is particularly difficult to deal with, because morbidities associated with procedures for chronic pain reduction may be permanent and significant.

For example, a patient suffering from chronic leg pain may be in continuous pain causing the patient a very poor quality of life. However, an invasive surgical procedure to sever the nerve, and hopefully thereby remove the pain, may have drastic consequences. For example, the wrong nerve or nerve bundle may be cut, such that the pain is not eliminated, and severing the nerve may remove feeling, sensation, or muscular control from some other undesired area, or even causes immobility or other undesired consequence.

In another example, a patient may be undergoing a medical procedure over the period of days or weeks that is very painful. One example may be the stretching of a leg bone in a patient. The procedure may last weeks or longer, and be painful over the entire procedure. It may be desirable to reduce or eliminate the pain sensed from the nerves of the affected area without systemic activity. For example, a systemic drug may be undesirable, because the level of the drug necessary for the reduction of the pain may produce systemic side-effects that are undesired for the time period of the procedure.

Providing HIFU for temporary or permanent pain reduction in accordance with the present invention reduces or eliminates some of the morbidities associated with invasive nerve severing procedures, systemic drug delivery, or other pain reducing or eliminating alternatives. Methods in accordance with the present invention provide for long-term pain reduction without long term use of drugs. Further, embodiments of the present invention provide for more accurately targeting the nerves and/or nerve bundles specific to the pain.

FIG. 1A illustrates a method 100 of pain reduction in accordance with embodiments of the present invention. The method 100 involves targeting 110 the focal zone of an ultrasound transducer on a nerve. Ultrasonic energy is provided 120 at a first level to the nerve using the ultrasound transducer, the first level sufficient to stimulate the nerve. The operator or surgeon then verifies 130 that the stimulated nerve is a nerve desired for the reduction of pain. After positive verification, ultrasonic energy is provided 133 at a second level to the nerve using the ultrasound transducer, the second level sufficient to cause nerve dysfunction.

For example, providing 120 high intensity focused ultrasound at a first level to the nerve sufficient to stimulate the nerve may involve providing a continuous wave of ultrasound energy from the ultrasound transducer, starting at a zero or quiescent amplitude, and slowly increasing the amplitude until verification 130 that the stimulated nerve is a nerve desired for the reduction of pain. Verification 130 may involve, for example, having the patient in a conscious or semi-conscious state and asking the patient when the stimulation from the ultrasonic energy is felt, and asking the patient if the stimulation is at the same location as the pain for which cessation is desired. In another method, a measurement of neural activity corresponding to the pain may be performed, or a measurement of an electrophysiological signal associated with the pain may be performed distally from the target area of the focal zone of the ultrasound transducer.

Once verified 130, providing 133 ultrasonic energy at a second level to the nerve sufficient to cause nerve dysfunction may involve increasing the amplitude of the ultrasonic energy until the nerve is made temporarily dysfunctional. In another embodiment, the energy level of the ultrasonic transducer is raised to the level of denaturing the nerve, causing permanent nerve dysfunction. Denaturing the nerve may be accomplished by denaturing the collagen in and/or around a nerve and/or nerve bundle. The collagen may be denatured from the heating effect of the ultrasonic energy. After cooling the collagen may congeal into a barrier sufficient to stop nerve re-growth. Delivering ultrasonic energy at a level below denaturization, but above a level sufficient to disrupt the nerve response, may provide for temporary elimination or reduction of the nerve response, and therefore pain cessation or reduction by the patient.

Embodiments of the present invention involve placing a nerve to be treated in the focal zone of an ultrasonic wave front emitted by ultrasound transducer, such as by adjusting the focus of a phased-array ultrasound transducer using a controller. Focusing and targeting of ultrasound transducers are further described in U.S. Pat. Nos. 4,484,569 and 4,858,613, and 5,117,832, which are hereby incorporated herein by reference.

A method of pain reduction in accordance with embodiments of the present invention involves targeting the focal zone of an ultrasound transducer on the nerve. A first level of ultrasonic energy is provided to the nerve using the ultrasound transducer, the first level sufficient to stimulate the nerve. Ultrasound interaction with nerves is further described in U.S. Pat. Nos. 5,807,285, and 6,656,136, which are hereby incorporated herein by reference.

A verification is made that the desired nerve is being stimulated by the first level of ultrasonic energy. For example, the patient may be asked to confirm that the ultrasonically stimulated nerve corresponds to the pain that is affecting the patient. Subsequent to verifying the stimulated nerve is the nerve desired for the reduction of pain, a second level of ultrasonic energy is delivered to the nerve using the ultrasound transducer, the second level of ultrasonic energy sufficient to cause nerve dysfunction. The patient may be placed into a non-conscious state prior to delivering the second level of ultrasound energy to mitigate any pain associated with the higher level of energy delivery.

Several mechanisms of ultrasound tissue interaction may contribute to bioeffects and nerve dysfunction. Generally these mechanisms are separated into thermal effects and mechanical effects. Ultrasound induced events such as cavitation, micro-streaming, heating through absorption, and free radical production can all produce bioeffects.

Cavitation occurs when the peak rarefactional pressure exceeds a threshold where tissue is stressed to the point of failure, yielding a cavity that may contain gas and vapor. A significant amount of mechanical energy is released when the cavity collapses.

Absorption is the process by which mechanical energy is converted into heat. Absorption, along with reflection and scattering, lead to attenuation of ultrasound when propagating through tissue. Absorption in tissue is generally specified via an attenuation coefficient in units of dB/cm/MHz. At high acoustic intensities, such as those present in therapeutic ultrasound, attenuation is highly non-linear and standard attenuation coefficients are not reliable for calculations. Therefore determining absolute intensity levels and dosage is difficult and typically established empirically.

Because of its unique properties in soft tissue, ultrasound can be brought to a tight focus at a distance from its source. If sufficient energy is radiated within the ultrasound beam, cells located in the focal volume can be rapidly heated, while intervening and surrounding tissues are spared. Surrounding tissues are unaffected in the unfocused portion of the ultrasound beam because the energy is spread over a correspondingly larger area and associated heating is minimized.

Whereas ultrasound intensities on the order of 0.1 Watts/cm squared are employed in diagnostic imaging applications, intensities in excess of 1,000 Watts/cm squared are typical in high-intensity focused ultrasound (HIFU) applications. At the focal point, these high intensities result in large, controlled temperature rises within a matter of seconds.

Figure 1B:
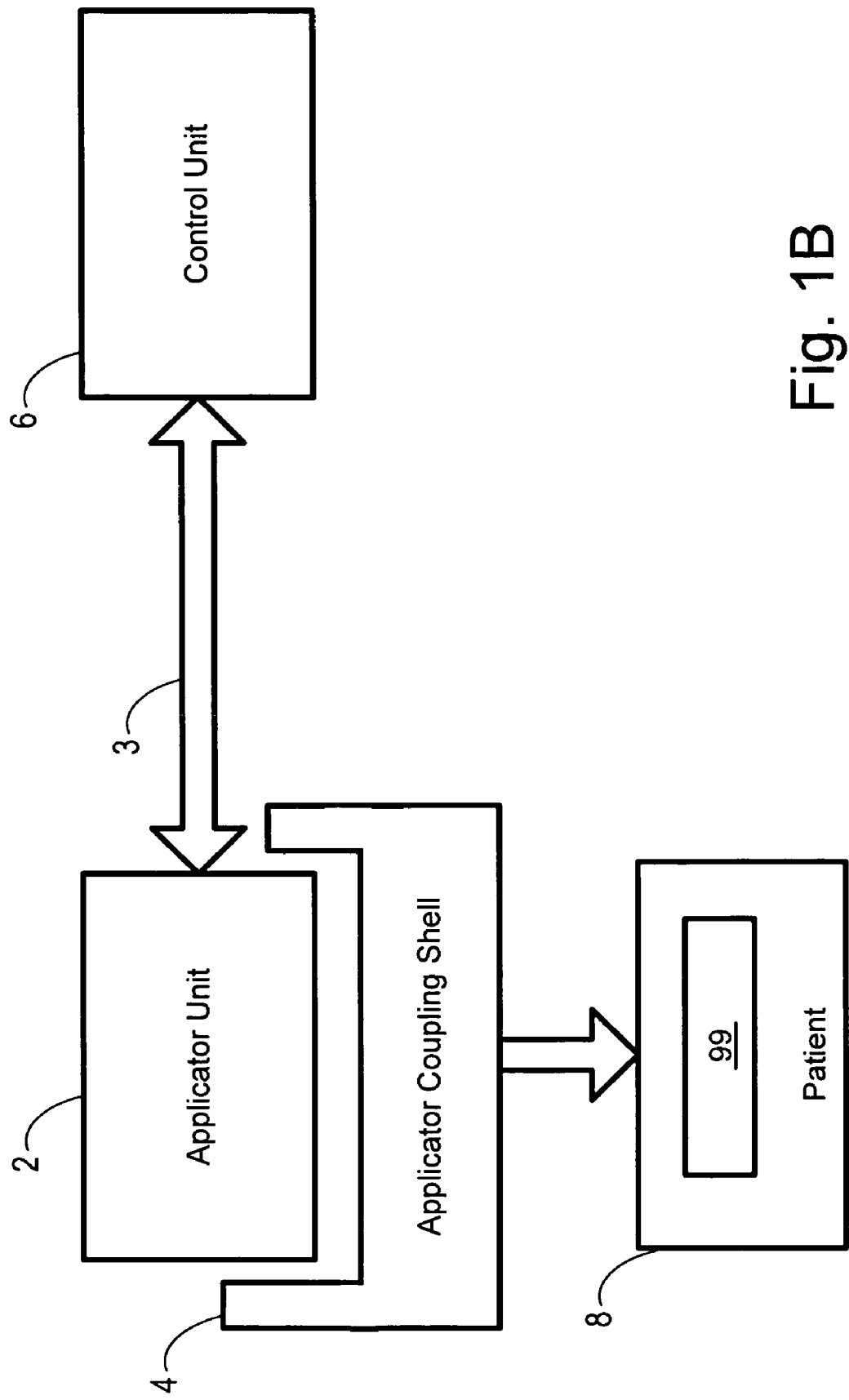
FIG. 1B is a schematic block diagram of the primary components employed in an embodiment of a system useful for pain reduction in accordance with embodiments of the present invention.

FIG. 1B shows the main components of an ultrasonic system suitable for use in implementing the present invention. As illustrated in FIG. 1B, a hand-held applicator unit 2 is positioned over a nerve 99 in a patient 8. Included with the hand-held applicator unit is a generally single-use, pre-sterilized cover and acoustic coupling shell 4 that slips over applicator 2. A control unit 6 implements algorithms to facilitate the method and is coupled to applicator 2.

Figure 2:
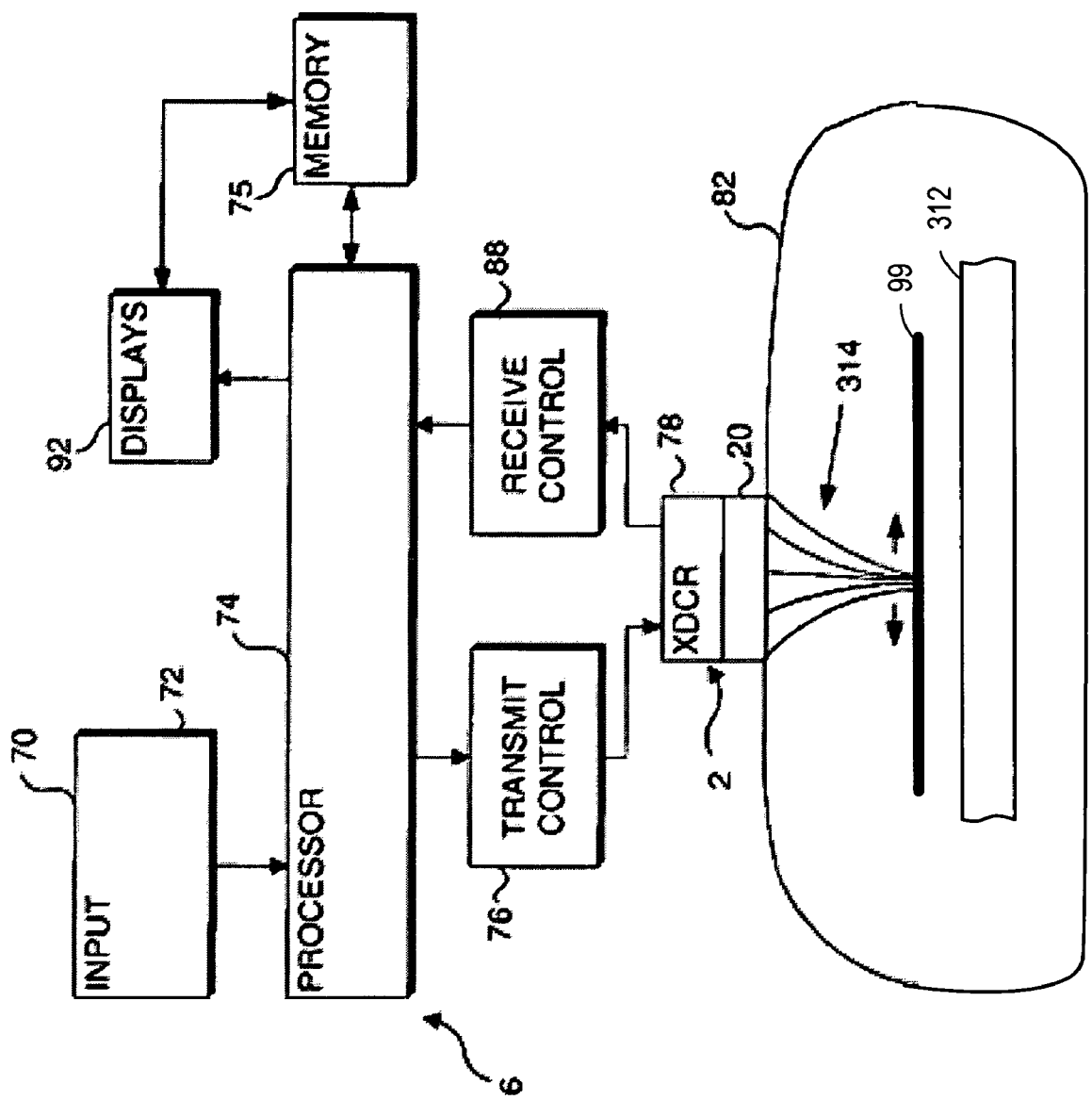
FIG. 2 is a schematic diagram illustrating how the present invention is employed for reducing or eliminating pain by causing nerve dysfunction.

Referring now to FIGS. 1B and 2, the user enters various conventional scan and control parameters into an input unit 70, which typically includes user input devices 72, such as a keyboard, touch-screen, or other input device. The input unit 70 is connected to a processing system 74, which will typically comprise a plurality of microprocessors and/or digital signal processors. Processing system 74 may, however, also be implemented using a single processor of sufficient speed to handle the various tasks described below. A conventional memory 75 will normally be included in the system to store, among other data, transmission control parameters and imaging data generated in any given implementation of the present invention.

Processing system 74 sets, adjusts, and monitors the operating parameters of a conventional transmission and control circuit 76. Control circuit 76 forms a transmit ultrasonic waveform by generating and applying electrical control and driving signals to an ultrasound transducer 78, which may include an array of individually controllable piezoelectric elements. As is well known in the art, the piezoelectric elements generate ultrasonic waves when electrical signals of a proper frequency are applied to them; conversely, when receiving reflected ultrasonic waves, they generate electrical signals corresponding to the mechanical vibrations caused by the returning ultrasonic waves.

Transducer 78 is positioned against a portion 82 of the body of a patient, and by varying the phasing, amplitude, and timing of the driving signals for the transducer array elements, ultrasonic waves are focused to form a transmit beam 314 of high-intensity ultrasound. For example, in FIG. 2, the nerve 99 is illustrated in the focal zone of the transducer 78. A vessel 312 is illustrated as following generally the same path as the nerve 99, which will be described in more detail below.

As will be clear from the description of the present invention below, it is not necessary for the system to include an imaging capability. However, the provision of an imaging capability, including pulse-echo lines of interrogation that are not displayed as images, in the present invention should assist a user to more accurately locate a desired nerve for which dysfunction is desired. It is recognized that a full display of the insonified target site is not required.

Nonetheless, since imaging of a target site is preferable and will employ echo processing (for example, Doppler), FIG. 2 also illustrates a reception controller 88, which will include conventional amplification and signal conditioning circuitry as needed. Reception controller 88, all or part of which is normally integrated into processing system 74, converts the ultrasonic echo signals (which are typically at radio frequencies, on the order of a few to tens of megahertz) into lower frequency ranges for processing and may also include analog-to-digital conversion circuitry. The processing includes, as needed, such known signal conditioning as time-gating, gain compensation, Doppler frequency shift processing, and diffraction compensation, in order to help identify echo signals from any selected focal region. The type of conventional signal processing needed (if any) will in general depend on the particular implementation of the present invention employed and can be implemented using known design methods.

Note that it is not essential, according to the present invention, that the transducer 78 be used externally, relative to the patient's body. It is also contemplated that the transducer may be maneuvered inside a patient's body, and the beam focused on a nerve from inside the body. For example, a transesophageal probe, laparoscopic, or other probe inserted into a body cavity, such as the abdomen, vagina or rectum can be used to practice the present invention. A suitably designed probe inserted into an open body cavity or via minimally invasive means could be used to treat pain in surgical or trauma care situations. Yet, most of the following discussion is directed to a embodiment of the present invention in which the transducer is intended to be used externally, as an example for purposes of clarity of description.

A display system 92 may also be included in order to display information concerning transmission power, time, focus data, etc. The display system will include known circuitry for scan conversion and for driving the display, as needed. These circuits are well known and therefore need not be specifically illustrated or described further to provide an enabling disclosure.

Figure 3:
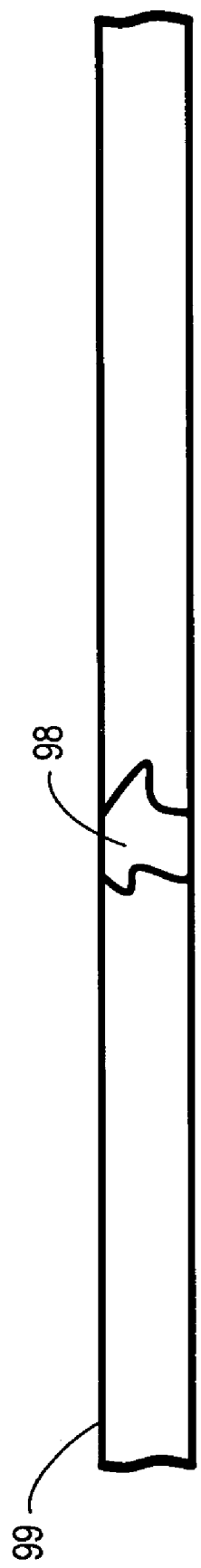
FIG. 3 schematically illustrates a collagen seal produced by the present invention to block the nerve of FIG. 2.

FIG. 3 illustrates the result of an insonification of the nerve 99 using the present invention, where the nerve has been denatured such that nerve re-growth is blocked. As the focal point of transmit beam 314 (see FIG. 2) is targeted to the area of nerve using conventional focusing and beam-steering techniques, and a level of ultrasound energy sufficient to denature the nerve is delivered, the nerve will denature and form a blockage 98. In effect, the collagen in the tissue "melts" and flows within the area of the focal zone. When the collagen cools, it forms a "patch" that seals the nerve shut, in this case permanently blocking regrowth of the nerve along the previous pathway and re-establishing activity. If a lower level of ultrasonic energy is used, the block 98 may not be formed, but the nerve may be disrupted such that nerve activity is temporarily disrupted, stopping pain signals from being delivered to the brain. If no blockage 98 is formed, the pathway remains for the nerve to re-establish the signal pathway after a period of time, such as, for example, one to two weeks.

Figure 4:
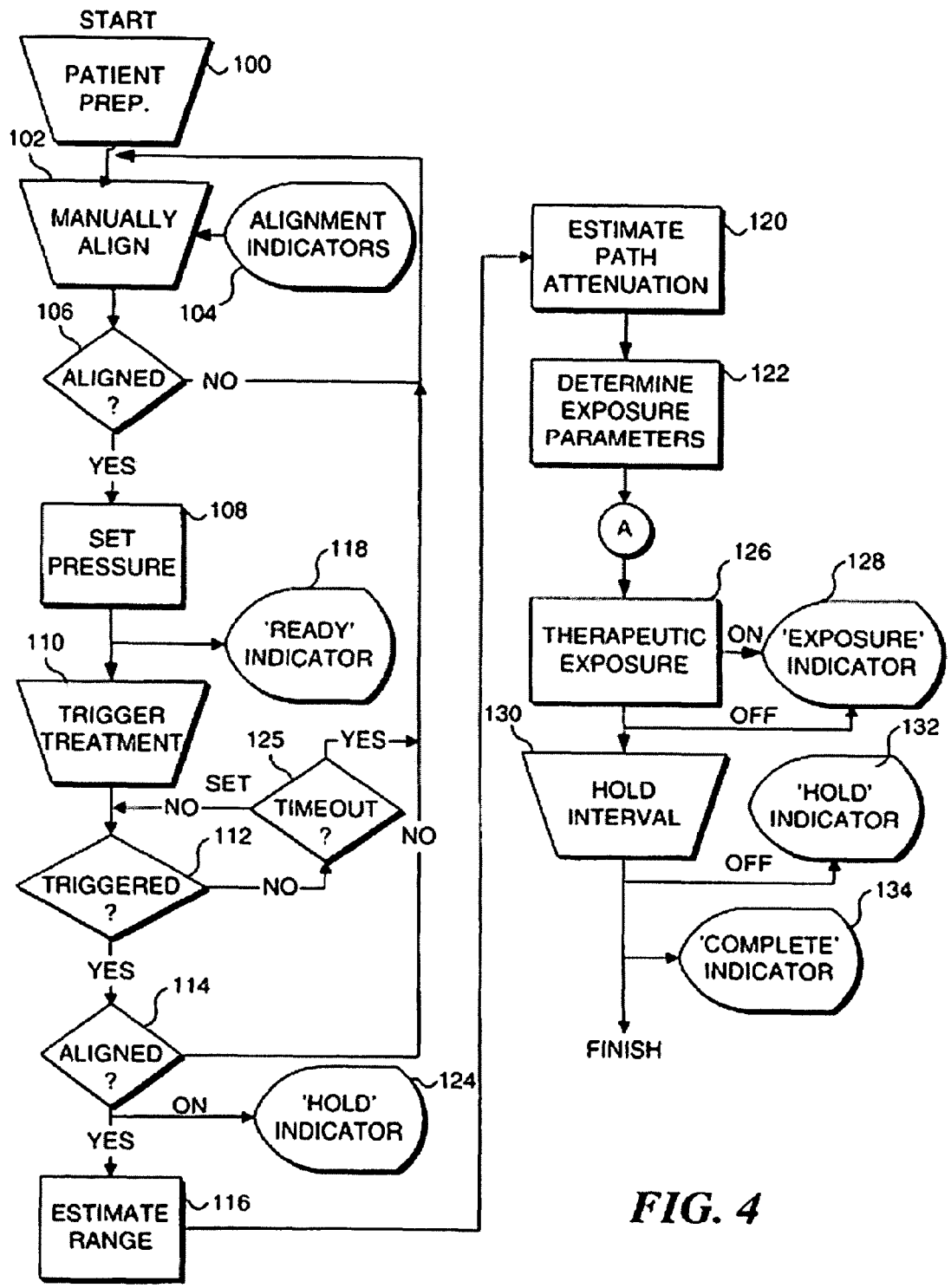
FIG. 4 is a flow chart illustrating the logical steps followed during an embodiment of methods that provide ultrasonic energy used to cause one or more nerves to become dysfunctional in accordance with the present invention.
Figure 5:
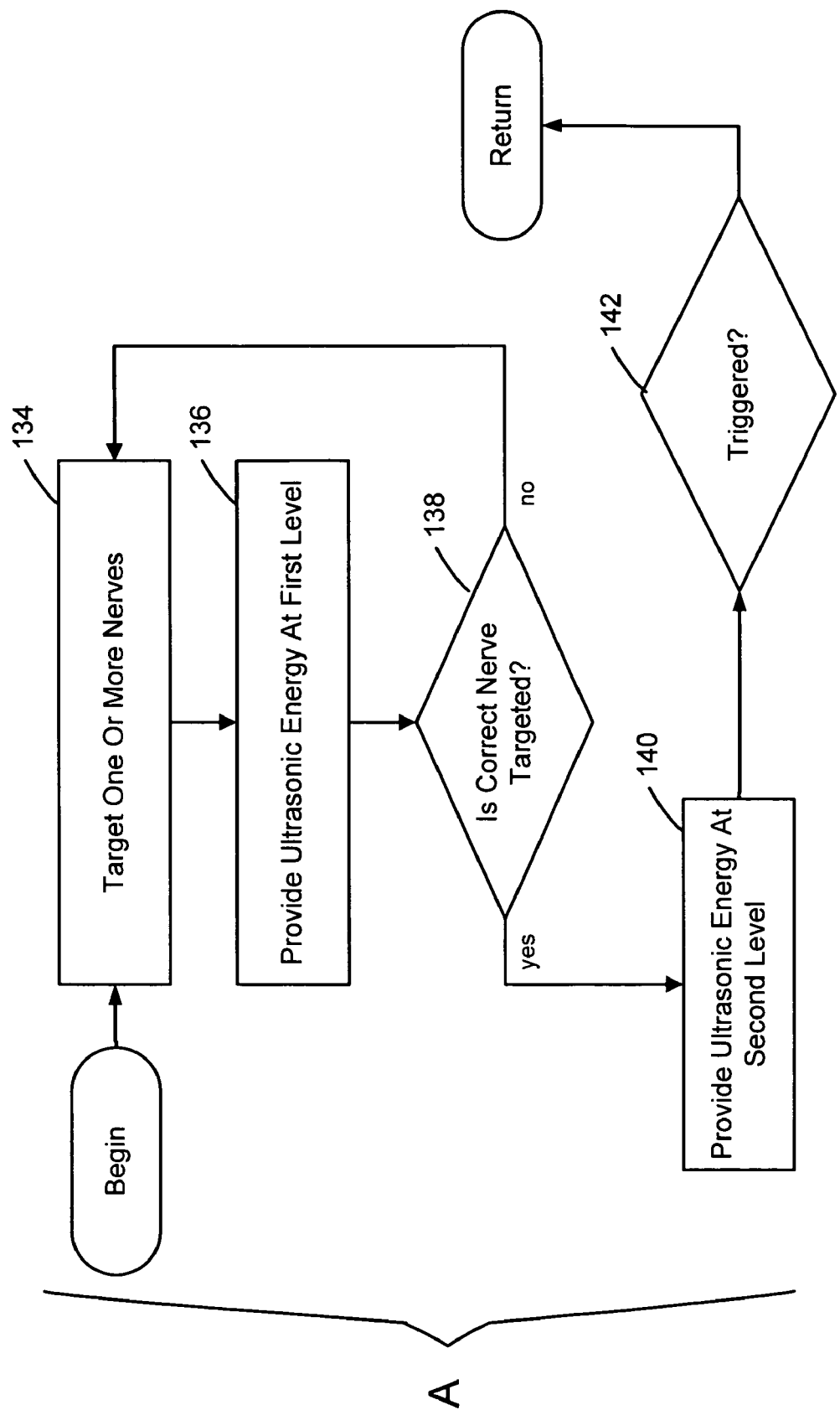
FIG. 5 is a flow chart illustrating the steps employed for verifying that the desired nerve is targeted during the method of FIG. 4 in accordance with an embodiment of the present invention.

Steps carried out in methods in accordance with the present invention are shown in FIGS. 4 and 5, which are further described below. These steps represent one embodiment of the present invention, but do not represent all alternatives that might be employed to achieve nerve dysfunction.

Steps in the method for nerve dysfunction described here include: (1.) Positioning an ultrasound generating source on a patient such that the source is targeted at an area including the nerve to be made dysfunctional; (2.) delivering a first level of ultrasonic energy, directed substantially toward the nerve to be treated; (3.) Verifying that the correct nerve is targeted; and 4) delivering a second level of ultrasonic energy, directed substantially toward the nerve, thereby causing nerve dysfunction. For example, the second level of ultrasonic energy may deliver an acoustic energy density (measured at the approximate location of the nerve), in excess of 10 joules/sq. cm, but generally less than several thousand joules/sq. cm., whereas the first level of ultrasonic energy is typically less than 10 joules/sq. cm, and may be less than 100 joules/sq. cm.

Additional steps of the method described below employ the apparatus in a manner that facilitates ease of use and provides the safety and efficacy desired. Referring now to FIG. 4, the method described includes a series of manual steps (operator actions) and automated steps. The automated steps are carried out as control processes or algorithms executed by one or more processors and other hardware in accord with machine instructions executed by the one or more processors. It is understood that variations in the order of these steps, and in the total complement of steps implemented, is possible in alternative embodiments. Steps as shown in FIG. 4 are described as follows.

Figure 8A:
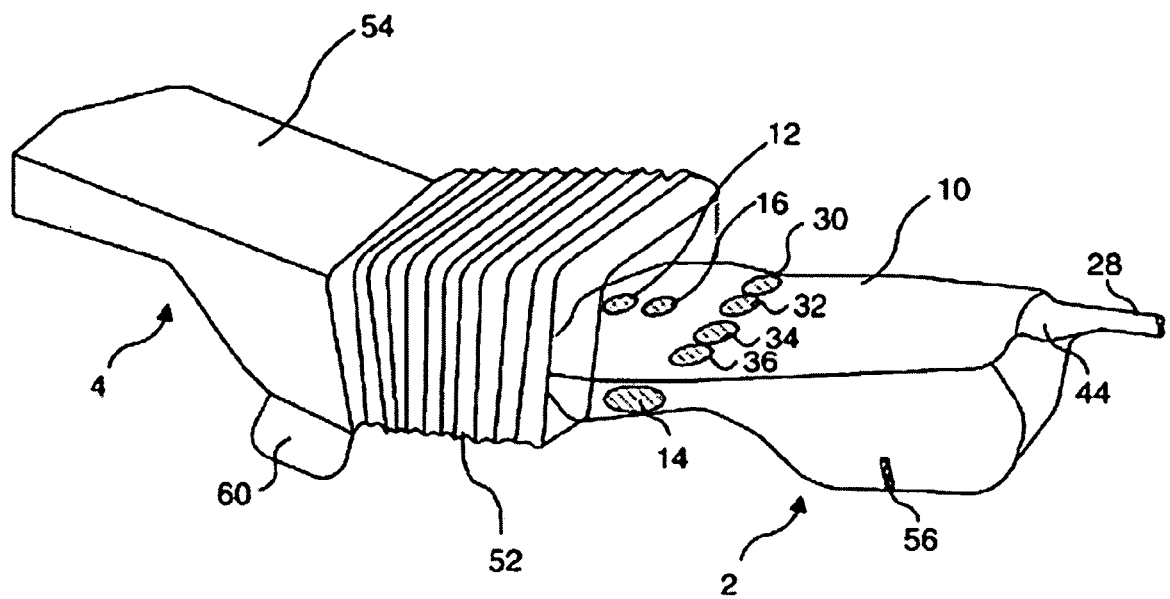
FIG. 8A is a schematic isometric view of an embodiment of the applicator that uses a disposable shell.
Figure 8B:
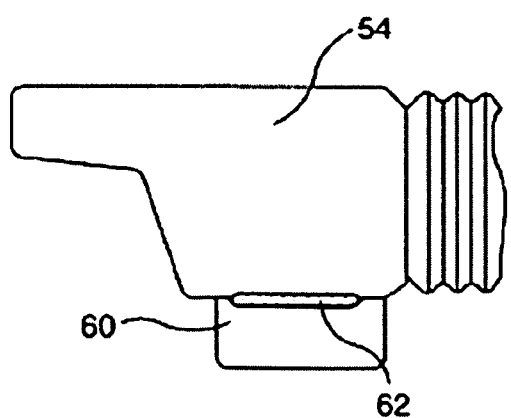
FIG. 8B is a side view of the disposable shell of FIG. 8.

In a step 100 labeled Patient Preparation, the operator positions the patient and the apparatus so that the applicator unit is conveniently positioned over the nerve area. Shell 4 is removed from its sterile package and fitted onto applicator unit 2, and gel sealing tab 60 (shown in FIGS. 8 and 8*b*) is removed, exposing the gel 62.

A step 102 labeled Manually Align is then carried out. The operator marks a location on the patient's skin with a suitable marking device (e.g. a surgical marker), drawing a line substantially perpendicular to the perceived direction of the nerve fiber or nerve bundle. It is the purpose of this marking to estimate the longitudinal location of the nerve bundle. Other techniques for locating the nerve are discussed below.

Nerve bundles sometimes follow the paths of vasculature to the extremities. Therefore, if a nerve or nerve bundle associated with the patient's pain travels along the path of a vein or artery, the vein or artery may be used to align the transducer to the general area of the nerve. In another embodiment, the nerve may be more precisely located by targeting capability provided by a visual indicator of the focal zone being provided on an ultrasonic image.

Also within step 102, the operator places the device over the nerve location, aligning fiducial mark "56" (shown in FIG. 8) with the line that was drawn on the patient's skin. The axial alignment indications are, in an embodiment where the nerve bundle travels along the path of a vein or artery, derived from two ultrasonic pulsed Doppler interrogations for the vein or artery. Use of an ultrasonic transducer 20 enables the same ultrasonic transducer to be employed to produce an imaging beam and the HIFU beam for both a pulse-echo targeting mode and a therapeutic mode.

Figure 6:
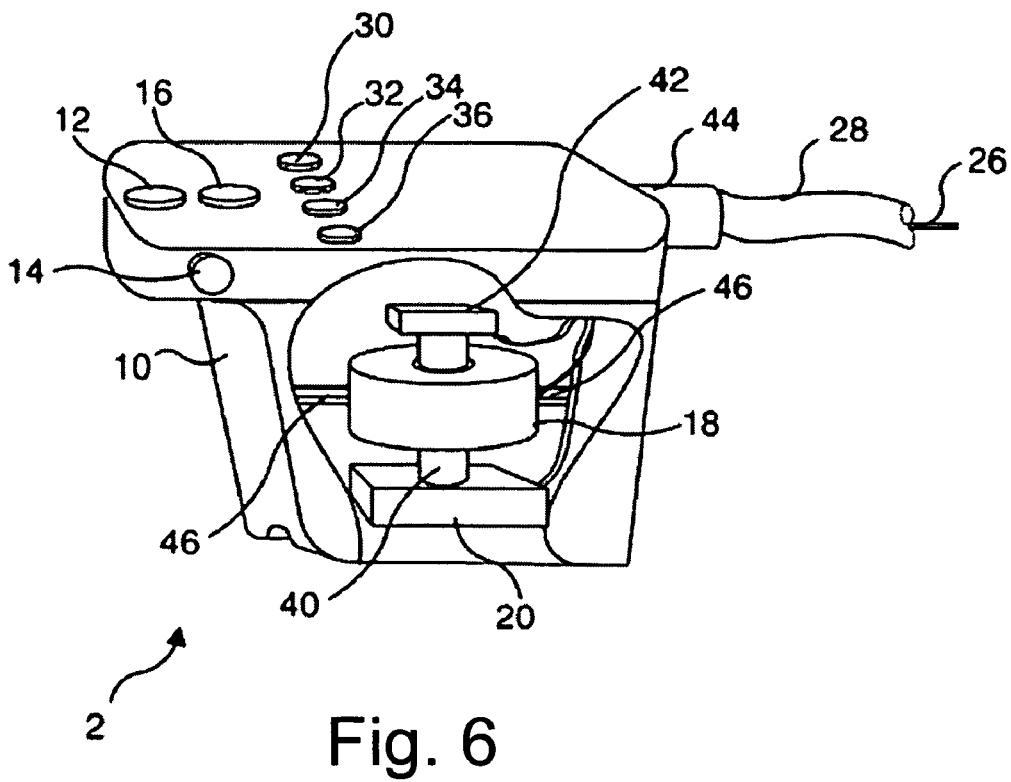
FIG. 6 is a cutaway isometric view of the applicator.
Figure 7:
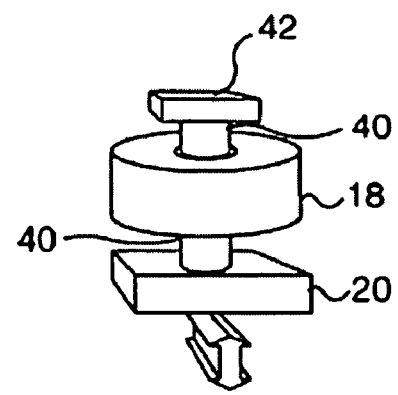
FIG. 7 is an isometric view showing the force sensing transducer, force generator, and ultrasonic array of the applicator.

FIG. 6 and FIG. 7 show one embodiment of applicator unit 2 suitable for use in accordance with the present invention. The applicator unit includes an outer housing 10 having an ergonomically considered shape so that it can be conveniently hand held. The outer housing is best fabricated from an injection moldable plastic material such as ABS or the like. The operator grasps the outer housing of the applicator unit so as to enable a control push-button 14 to be accessible and indicators 12, 16 and 30, 32, 34, and 36 to be visible to the operator. Positioning the applicator unit at the appropriate location over the nerve area and activation of a treatment cycle are readily accomplished. The operator simply refers to the indicators to determine when the applicator unit is properly positioned and ready for use. Indicators 12 and 16 are used to indicate when alignment of the applicator unit with the longitudinal axis of the nerve to be affected has been achieved. Indicators 30, 32, 34, and 36 display the state of operation and instruct the operator with respect to holding the applicator in place as described in detail later in this description. Control 14 when pressed, activates the treatment cycle, thus initiating a sequence of operations that determine ultrasonic scan parameters (exposure time, scan pattern, intensity, focal range, etc.).

As shown in FIG. 6, ultrasonic array assembly 20 is held within outer housing 10 on a shaft 40, in a bearing assembly within a force transducer 18, so as to permit movement of the ultrasonic array assembly to and away from the patient. Shaft 40 passes through the bearing assembly provided within a force generator 18 and terminates at a contacting force sensing transducer 42. Force generator 18 comprises an electromagnetic solenoid that is rigidly supported and mounted within housing 10 by structural members 46. The face of ultrasonic array assembly 20 is in contact with the appropriate location on the body of the patient and is thus capable of applying a substantially compressive, controllable force on the tissue structures with which it is in contact. The force applied by the ultrasonic array assembly is produced at least in part by controllably energizing force generator 18. Ultrasonic array assembly 20 preferably operates in a multiplicity of modes; however, separate ultrasonic transducers can instead be provided for some or all of the functions performed in a different design within the scope of the present invention.

In the illustrated embodiment, electrical connections comprising wires 26 are routed within the outer housing 10 and out in a sealed bushing 44 that mounts a cable 28 to the control unit 6. Cable 28 is sufficiently long, on the order of 10 feet in length, so that the control unit may be conveniently located at a distance from the patient and operator location.

Applicator unit housing 10 is shaped to be used with a slip-on, generally single-use protective applicator shell 4 (illustrated schematically in FIG. 1B). The shell employed in the embodiment is shown in greater detail in FIGS. 8A and 8B. Shell 4 has side walls 54 that are fabricated from a generally optically transparent, semi-rigid plastic material. A skirt 52 extends from the rear of the shell and is pleated so that in preparing for use of the applicator unit, an operator can grasp the skirt and extend it sufficiently to protect a sterile area of the patient from coming into contact with cord. The protective shell is packaged in a sterile condition. The shell is fabricated from a flexible plastic material having low acoustic absorption characteristics. A fiducial mark 56 is provided on a side of the applicator unit and visible through the optically transparent material of the protective shell. This fiducial mark is employed to visually align the applicator unit with a position on the patient at which the applicator unit will be used to affect a nerve.

Sterile, generally gas free acoustic coupling gel 62 is deposited in a patch on the bottom of flexible bottom 58. Prior to use, the gel is held in place and sealed by semi-sticky adhesive coated tab 60. Tab 60 is removed by the operator just prior to use, thereby exposing the gel so that it provides a good acoustic coupling with the surface of the patient's body. Protective applicator shell 4 thus provides a sterile barrier over the multi-use applicator unit and conveniently provides a pre-determined amount of a specific appropriate acoustic coupling medium. Although not shown, it is contemplated that the bottom of the interior cavity of the shell may also include a layer of acoustic coupling gel to ensure good acoustic coupling between the applicator unit through the protective, applicator coupling shell.

Figure 9:
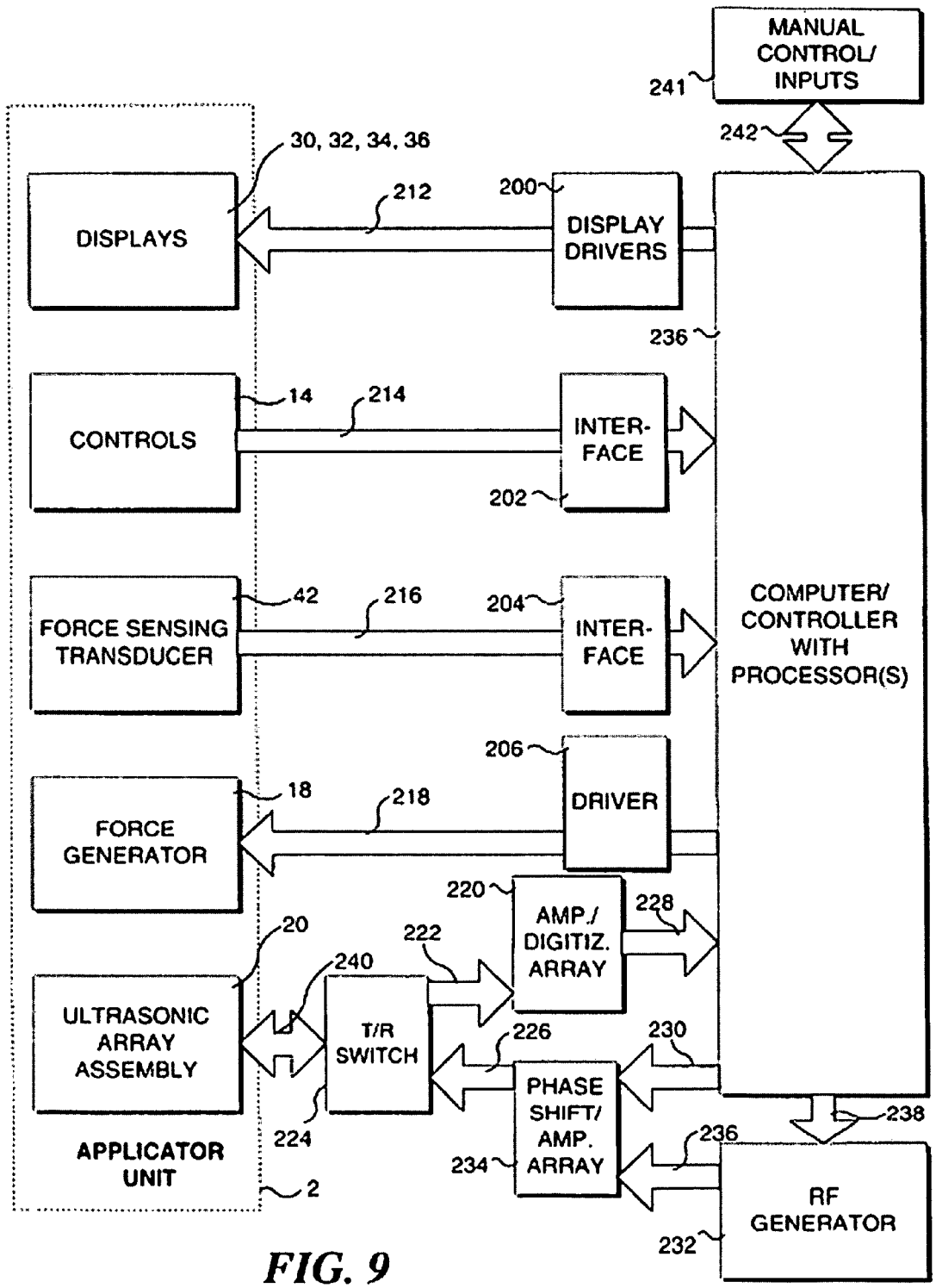
FIG. 9 is a schematic system block diagram depicting modules included in the applicator and control unit.

With reference to FIGS. 1B, 6, and 9, applicator unit 2 is connected to control unit 6. Power supplies, signal processing components, and control and RF power generation components are housed within control unit 6. FIG. 9 is a system block diagram illustrating the modules disposed, in the embodiment, within the applicator unit 2, as well as the modules (for example other modules that are not in the applicator unit) disposed in the control unit 6. In this embodiment, control unit 6 is packaged in a small, self-contained pole- or cart-mounted enclosure that derives its input power from a standard AC line power service (not shown). Power supplies with the unit are designed to assure low leakage currents for patient safe operation.

In the embodiment the architecture of control unit 6 is based on a programmable processing unit which processes various signals and controls a number of functional modules. A microprocessor is well suited to perform the computation and control functions required. Applicator unit 2 is coupled to control unit 6 by a plurality of signal paths 212, 214, 216, and 218. Signal path 212 couples display drivers 200, which are controlled by a computer/controller 236, with indicators 30, 32, 34, and 36 on the applicator unit. Control button 14 on the applicator unit is coupled through signal line 214 to an interface 202 and thus to the computer/controller. Force sensing transducer 42 produces an output signal indicative of the force (i.e., the pressure) applied against the surface of the patient's tissues by the applicator unit, and this signal is conveyed by signal lines 216 to an interface 204, which provides the signal to the computer/controller. In response to the magnitude of the monitored force, the computer/controller produces a control signal applied to a driver 206, which provides the current signal used to energize force transducer 16, to determine any additional force that it generates to achieve a desired pressure on the site of the nerve.

Signal lines 240 couple ultrasonic array assembly 20 to a transmit/receive switch 224. The transmit/receive switch determines the operational mode of the ultrasonic array assembly under the control of the computer/controller. When operating in a diagnostic mode in which the ultrasonic array assembly is producing an imaging ultrasound beam, the signal corresponding to the echo reflected received by ultrasonic array assembly 20 from tissue and other structures is conveyed through transmit/receive switch 224 and through signal lines 222 to an amplifier digitizer array 220. The output signals from the amplifier digitizer array are conveyed to computer/controller 236 through signal lines 228. When the ultrasonic array assembly is generating either the imaging beam or the HIFU beam, it is responding to signals received from an RF generator 232 that is coupled to a phase shift/amplifier array 234 by signal lines 236, and to a control signal provided by the computer/controller and conveyed to the phase shift/amplifier on a signal line 230. The output of the phase shift/amplifier is conveyed on signal lines 226 to transmit/receive switch 224, and thus, to ultrasonic array assembly 20 through signal lines 240. Manual control inputs 241 are coupled to computer/controller 236 through signal lines 242.

A number of variously advantageous transducer configurations may alternatively be employed in this invention. Possibilities include, but are not limited to: (1.) Configurations wherein therapeutic and, pulse-echo Doppler functionality are accomplished by the same ultrasonic transducer or by separate ultrasonic transducers; (2.) Configurations wherein the ultrasonic transducer is either of a fixed focus type, or a segmented electrically selectable macro element array, or a phased array, or a linear array, or an annular array; (3.) Configurations where a large focal spot 412 (e.g. a focal spot produced by a transducer having an aspheric shape), or those in which a tightly focused spot is produced; and, (4.) Configurations wherein the ultrasonic transducer is mechanically positioned (or scanned), or those in which it is fixed in one position.

An aspheric ultrasonic transducer configuration has the advantage of covering a large treatment area around the nerve without the complication of electronic or mechanical beam steering. Covering a large area (i.e., overscanning) may be desired in order to ensure that the actual site of the nerve is treated, for example if the entire nerve bundle is designated for treatment and collateral nerve damage is not of significant concern.

Referring back now to FIGS. 4 and 5, in the alignment sequence of steps 102, 104, 106, phased array ultrasonic transducer 20 may send and receive pulsed Doppler signals. Pulsed Doppler signals may be used to align the transducer along the path of a vessel, if it is convenient to use vessel location information to help identify nerve structures that may travel along the path of the vessels. A verification step 106 is performed to verify that the desired nerve is being targeted, as described earlier. The system then proceeds to a step 108 labeled Set Pressure, wherein the pressure over the target is set and controlled within a predetermined range using force generator 18 (FIG. 6) and force sensing transducer 42. In this embodiment, the weight of the applicator unit is purposefully made to be in a range where additional pressure applied by the operator to hold the unit firmly in place is reduced. This useful weight is about 1 lb (0.45 kg) or more. Force generator 18 is activated and controlled such that applied pressure to the target area partially compresses the area of the nerve.

In this embodiment, when the system has completed the pressure application cycle described above, indicator 32 (FIG. 6), which is marked "READY" on the applicator unit is illuminated (see block 118 FIG. 4), indicating to the operator that a treatment cycle may be manually initiated (triggered) by pushing control button 14. The system is in a wait state as indicated in a decision block 112 in FIG. 4, until a manually triggered treatment cycle is detected. With the detection of a triggered treatment cycle, axial alignment is verified in a step 114 by generally repeating the logical test described at step 102.

A step 116 then makes a ranging measurement to estimate the acoustic path length between ultrasonic transducer assembly 20 and the target. A step 120 estimates the acoustic attenuation at the therapeutic frequency between ultrasonic transducer assembly 20 and the target nerve, using techniques known in the art. In this embodiment, a simplified approach is employed wherein an estimated dimension is used to access data in a look-up table of attenuation values. Attenuation values in the table are predetermined by empirical measurement. Alternatively, more sophisticated A-Mode attenuation measurements may be employed.

A step 122 determines the therapeutic ultrasound exposure parameters to be employed. For example, the attenuation estimate, and optionally, patient parameters (e.g., size and weight), input at module 240 in FIG. 9, are used to access predetermined data and scan protocols in resident look-up tables. Ultrasound scan geometry, intensity and epochal exposure intervals are thus determined. For example, as described earlier, the patient may indicate when a level of ultrasonic energy is felt, and that level may be used to correspond to a look-up table or algorithmic calculation for both a first level (detection) and a second level (therapeutic) of acoustic intensity.

A step 126 carries out the therapeutic exposure cycle. It is generally desirable to hold the applicator unit in place, providing the established orientation and pressure for a period of time after the therapeutic exposure cycle. A hold interval 130 (FIG. 4) is selected to enable exposed tissue structures to cool, for example, a time period of approximately 1 minute. Following this time period, indicator 36 on the application unit (FIG. 6) marked "COMPLETE" is illuminated and the "HOLD" indicator is turned off, instructing the operator that the therapeutic treatment is completed and the device may be removed from the patient.

Methods in accordance with the present invention provide for verification that the correct nerve is being targeted using patient feedback such as verbal acknowledgement, observation of movement (or lack thereof, or electrophysiological or neurological measurement, such as by using the sequence depicted in FIG. 5. The sequence is inserted into the process flow of FIG. 4, in this embodiment, at a location marked "A."

In FIG. 5, the desired nerve is targeted 134. To detect the presence of the nerve in the focal zone, a relatively weak, first ultrasonic energy level pulse or wave is transmitted in a step 136. The operator observes in a decision step 138 whether a reaction of pain and/or uncommanded movement from the patient has occurred, indicating that a nerve structure has been stimulated. System logic then waits for a manually initiated trigger input in steps 140 and 142, prior to proceeding with therapeutic exposure at step 126 in FIG. 4.

If there is an indication that the wrong nerve, or too many nerves, are being targeted at decision 138, then targeting 134 is performed again after realignment of the transducer and/or by steering and/or focusing of the beam's focal zone. After the re-alignment targeting 134, step 136 is repeated until a determination is made that the correct nerve or group of nerves is being targeted, before triggering 140 treatment for nerve dysfunction. For example, the patient may be subjected to repeated pulses 136 and re-targeting 134 until the patient identifies that the targeted nerve is the one causing the patient's pain, as described above. In other embodiments, neural scans of the brain are performed, electrophysiology measurements are made, or other feedback is used to determine that the correct nerve tissue is targeted.

Step 102, which facilitates alignment of the applicator unit over the nerve area and targeting 134 of the therapeutic exposure, may be accomplished using several alternative approaches compared to that described above. It may be desired to employ an approach for targeting and aligning the applicator unit that is easy to implement and requires minimum operator instruction. Additionally, the approach should be robust and provide targeting of the nerve site with sufficient accuracy such that the nerve will reliably be included within the area of therapeutic exposure.

Each feature disclosed in this specification (including any accompanying claims, abstract, and drawings), may be replaced by alternative features having the same, equivalent or similar purpose, unless expressly stated otherwise. Thus, unless expressly stated otherwise, each feature disclosed is one example only of a generic series of equivalent or similar features.

While embodiments of the present invention have been shown and described herein, it will be obvious to those skilled in the art that such embodiments are provided as examples only. Numerous variations, changes, and substitutions will be apparent to those skilled in the art without departing from the invention. Accordingly, it is intended that the invention be limited only by the scope of the appended claims.

What is claimed is:

1. A method of pain reduction, comprising:
providing an ultrasound transducer having a focal zone;

administering a first level of anesthesia to a patient, the first level of anesthesia sufficient to place the patient into a conscious state of sedation;

targeting the focal zone of the ultrasound transducer on a nerve of the patient;

providing ultrasonic energy to the nerve using the ultrasound transducer, the ultrasonic energy beginning at a zero or quiescent level, and increasing to a first level of ultrasonic energy to the nerve, the first level sufficient to stimulate the nerve and insufficient to cause nerve dysfunction;

verifying the stimulated nerve is a nerve desired for the reduction of pain using a response of the, stimulated nerve from the first level of ultrasonic energy, wherein the response of the stimulated nerve is determined by the patient acknowledging via a conscious action that the stimulated nerve is the nerve desired for the reduction of pain;

recording the first level of ultrasonic energy provided;

associating the recorded first level of ultrasonic energy to a corresponding second level of ultrasonic energy, the second level of ultrasonic energy sufficient to cause temporary or permanent nerve dysfunction;

administering, subsequent to verifying the stimulated nerve is the nerve desired for the reduction of pain, a second level of anesthesia sufficient to place the patient into an unconscious state; and providing, subsequent to verifying the stimulated nerve is the nerve desired for the reduction of pain, the associated second level of ultrasonic energy to the nerve using the ultrasound transducer.

2. The method of claim 1, wherein providing the second level of ultrasonic energy to the nerve comprises providing ultrasound energy from the ultrasound transducer at a level sufficient to denature the nerve, thereby causing permanent nerve dysfunction.

3. The method of claim 2, comprising providing a compressive force to the nerve as the denatured nerve congeals.

4. The method of claim 1, wherein the ultrasound energy from the ultrasound transducer is transcutaneously applied.

5. The method of claim 1, comprising generating an ultrasound image of the area proximate the nerve, wherein targeting the focal zone of the ultrasound transducer on the nerve comprises targeting the nerve using the ultrasound image.

6. The method of claim 1, wherein associating the recorded first level of ultrasonic energy to the second therapeutic level of ultrasonic energy comprises using the first level of ultrasonic energy to determine the second level of ultrasonic energy using a look-up table.

7. The method of claim 1, wherein associating the recorded first level of ultrasonic energy to the second therapeutic level of ultrasonic energy comprises using the first level of ultrasonic energy to determine the second level of ultrasonic energy using an algorithmic calculation.

8. A method of pain reduction, comprising:

targeting the focal zone of an ultrasound transducer on a nerve of a patient;

administering a first level of anesthesia to the patient, the first level of anesthesia sufficient to place the patient into a conscious state of sedation;

providing ultrasonic energy to the nerve subsequent to administering the first level of anesthesia, the ultrasonic energy beginning at a zero or quiescent level, and increasing to a first level of ultrasonic energy to the nerve using the ultrasound transducer, the first level sufficient to stimulate the nerve and insufficient to cause nerve dysfunction;

verifying the stimulated nerve is a nerve desired for the reduction of pain using a response of the stimulated nerve from the first level of ultrasonic energy, wherein the response of the stimulated nerve is determined by the patient acknowledging via a conscious action that the stimulated nerve is the nerve desired for the reduction of pain;

administering, subsequent to verifying the stimulated nerve is the nerve desired for the reduction of pain, a second level of anesthesia sufficient to place the patient into an unconscious state; and providing, subsequent to administering the second level of anesthesia, a second level of ultrasonic energy to the nerve using the ultrasound transducer, the second level of ultrasonic energy sufficient to cause nerve dysfunction, the second level of ultrasonic energy determined using the first level of ultrasonic energy.

9. The method of claim 8, wherein providing the second level of ultrasonic energy to the nerve comprises providing ultrasound energy from the ultrasound transducer at a level sufficient to denature the nerve, thereby causing permanent nerve dysfunction.

10. The method of claim 9, comprising providing a compressive force to the nerve as the denatured nerve congeals.

11. The method of claim 8, wherein the ultrasound energy from the ultrasound transducer is transcutaneously applied.

12. The method of claim 8, comprising generating an ultrasound image of the area proximate the nerve, wherein targeting the focal zone of the ultrasound transducer on the nerve comprises targeting the nerve using the ultrasound image.

* * * * *